(12) United States Patent
Ziegler et al.

(10) Patent No.: US 7,666,860 B2
(45) Date of Patent: Feb. 23, 2010

(54) MELT-FORMULATED, MULTI-PARTICULATE ORAL DOSAGE FORM

(75) Inventors: Iris Ziegler, Roetgen (DE); Johannes Bartholomaeus, Aachen (DE); Dieter Schateikis, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/366,583

(22) Filed: Mar. 3, 2006

(65) Prior Publication Data

US 2006/0147524 A1 Jul. 6, 2006

Related U.S. Application Data

(63) Continuation of application No. PCT/EP2004/009530, filed on Aug. 26, 2004.

(30) Foreign Application Priority Data

Sep. 4, 2003 (DE) ................ 103 41 264

(51) Int. Cl.
*A01N 43/10* (2006.01)
*A61K 31/43* (2006.01)
*A61K 9/14* (2006.01)
*A61K 9/127* (2006.01)

(52) U.S. Cl. ............... 514/210.01; 424/46; 424/450; 514/192

(58) Field of Classification Search ............ 514/210.01
See application file for complete search history.

(56) References Cited

U.S. PATENT DOCUMENTS

| 6,051,255 A | 4/2000 | Conley et al. |
|---|---|---|
| 6,783,773 B1 * | 8/2004 | Storm et al. ............. 424/468 |
| 2002/0015730 A1 | 2/2002 | Hoffmann et al. |
| 2003/0017208 A1 | 1/2003 | Ignatious et al. |

FOREIGN PATENT DOCUMENTS

| JP | S56-75437 | * | 6/1981 |
|---|---|---|---|
| JP | 05219885 A | * | 8/1993 |
| WO | WO 95/20946 | * | 8/1995 |
| WO | WO 95/28927 A1 | | 11/1995 |
| WO | WO 00/45888 A1 | | 8/2000 |
| WO | WO 01/66081 A2 | | 9/2001 |

OTHER PUBLICATIONS

International Search Report dated Aug. 6, 2005 (Three (3) pages).
German Search Report dated Jun. 3, 2004 (Two (2) pages).

* cited by examiner

*Primary Examiner*—Sreeni Padmanabhan
*Assistant Examiner*—Layla Soroush
(74) *Attorney, Agent, or Firm*—Crowell & Moring LLP

(57) ABSTRACT

A melt-formulated, multiparticulate, oral dosage form containing clavulanic acid and/or at least one physiologically acceptable salt thereof and at least one sucrose fatty acid ester and optionally further physiologically acceptable auxiliary substances; a process for producing such a dosage form, combination dosage forms with β-lactam antibiotics, and the pharmaceutical use thereof, e.g., for treating bacterial infections.

35 Claims, No Drawings

MELT-FORMULATED, MULTI-PARTICULATE ORAL DOSAGE FORM

CROSS REFERENCE TO RELATED APPLICATIONS

This application is a continuation of international patent application no. PCT/EP2004/009530, filed Aug. 26, 2004, designating the United States of America, and published in German as WO 2005/023216 on Mar. 17, 2005, the entire disclosure of which is incorporated herein by reference. Priority is claimed based on Federal Republic of Germany patent application no. DE 103 41 264.6, filed Sep. 4, 2003.

BACKGROUND OF THE INVENTION

The present invention relates to a melt-formulated, multi-particulate, oral dosage form containing clavulanic acid and/or one or more of the physiologically acceptable salts thereof and one or more sucrose fatty acid esters and optionally further physiologically acceptable auxiliary substances, to a process for the production thereof and to the use thereof.

Clavulanic acid, in particular in the form of potassium clavulanate, is frequently used in combination with a β-lactam antibiotic, such as for example amoxicillin, for the treatment of bacterial infections by Gram negative and Gram positive β-lactam-resistant pathogens. Due to the combination with clavulanic acid, which is capable of cleaving β-lactamases, these pathogens, despite initial resistance, again become sensitive to treatment with amoxicillin. This combination is used inter alia for the treatment of otitis media in children. Treatment involves the administration of different dose combinations of clavulanic acid to amoxicillin, with ratios of 1:4, 1:7 or 1:8 being the most common.

One major problem in the production of pharmaceutical preparations comprising clavulanate, preferably potassium clavulanate, is this compound's high susceptibility to hydrolysis. Even over the course of processing and storage of the compound under normal conditions (ambient temperature of 25° C. and 60% relative atmospheric humidity), increasing hydrolysis of the clavulanic acid occurs within a few hours to days, this being accompanied by an intense discoloration and release of $CO_2$.

Decomposition of the compound is accelerated as temperature and humidity increase and furthermore proceeds auto-catalytically, a cascade of different decomposition products possibly arising. This decomposition is described in greater detail in WO 94/16696.

As a consequence of this susceptibility to hydrolysis, when processing potassium clavulanate, which is conventionally already commercially available as a mixture with a grade of microcrystalline cellulose which is in a particularly desiccated form or with dry silicon dioxide, it is necessary both to exclude moisture (relative atmospheric humidity of the direct surroundings of less than 20%) and to keep the room or ambient temperature below 20° C.

Already known powders for suspension and film coated tablets are thus based on powder mixtures with silicon dioxide or on a dry compacted form of the clavulanate, wherein the auxiliary substances used must also be dried before use. When coating the tablets with a film, special low-moisture processes are used, as are for example described in WO 95/28927.

Since pellets are conventionally produced using aqueous solutions or with the assistance of lipophilic matrix materials, such a formulation method is not suitable for formulating mixtures containing clavulanate to yield pellets. Due to clavulanate's susceptibility to moisture, no aqueous solutions can be used and, due to the delaying action on active ingredient release which conventionally occurs, no lipophilic matrix materials may be used either. This is in particular contrary to the therapeutic goal, according to which rapid release and availability in the body are to be achieved.

SUMMARY OF THE INVENTION

The object of the present invention was accordingly to provide storage-stable dosage forms containing clavulanate in multiparticulate form, preferably as pellets, which preferably as pellets have no influence on the release profile of the active ingredient in comparison with, for example, a tablet obtained by dry compaction of the active ingredient powder, together with corresponding processes for the production of such a dosage form.

This object is achieved by providing a melt-formulated, multiparticulate, oral dosage form according to the invention containing clavulanic acid and/or at least one of the physiologically acceptable salts thereof and at least one sucrose fatty acid ester and optionally at least one further physiologically acceptable auxiliary substance.

These melt-formulated dosage forms according to the invention are multiparticulate, preferably in the form of granules or pellets, and are accordingly not obtained by any kind of spinning of a corresponding melt which contains active ingredient. The dosage forms according to the invention are accordingly melt-formulated with the exception of melt-formulation by any kind of spinning.

Due to the use of the sucrose fatty acid ester component, the dosage forms according to the invention do not exhibit any delaying action on active ingredient release. Accordingly, no or no additional delay to active ingredient release from the dosage forms according to the invention is observed due to the use of the sucrose fatty ester component.

Preferred dosage forms are those containing a physiologically acceptable salt of clavulanic acid, preferably potassium clavulanate or sodium clavulanate, and particularly preferably potassium clavulanate.

The active ingredient and all further components of the dosage forms according to the invention must be used in anhydrous form due to clavulanic acid's susceptibility to moisture. The dosage form according to the invention must itself also be protected from moisture.

The clavulanate, calculated as free acid, is present in the dosage forms according to the invention preferably in a quantity of 1 to 90 wt. %, very particularly preferably in a quantity of 30 to 80 wt. %, relative to the total weight of the composition of the dosage form.

The sucrose fatty acid esters used are preferably mono-, di-, tri- or polyesters of sucrose with at least one fatty acid, preferably a saturated or unsaturated $C_{12}$-$C_{22}$ fatty acid, particularly preferably a saturated $C_{12}$-$C_{22}$ fatty acid, or a mixture of at least two of the above-stated sucrose fatty acid esters, particularly preferably a mixture of mono- to polyesters of sucrose with fatty acids. Particularly suitable sucrose fatty acid esters are those which are derived from palmitic acid and/or stearic acid.

Sucrose fatty acid esters which are particularly suitable are those which exhibit an HLB value (hydrophilic-lipophilic balance value) of 1 to 3, preferably of 1 to 2, very particularly preferably of about 1. The HLB value is determined by the ratio of mono-, di-, tri- and/or polyesters in the sucrose fatty acid ester component. The sucrose fatty acid esters used are distinguished by a melting range in the range from 50 to 80°

C., preferably a melting range in the range from 55 to 65° C. Depending on the ratio of mono-, di-, tri- and or poly-esters in the sucrose fatty acid ester component, the melting range varies in the above-stated range.

Use of the sucrose fatty acid esters used according to the invention has no effect on the release of the active ingredient(s) from the dosage form according to the invention.

Sucrose fatty acid esters are approved food additives worldwide and are suitable for the production of pharmaceutical preparations for oral administration. They are commercially available products.

The sucrose fatty acid component is preferably present in the dosage forms according to the invention in a quantity of 1 to 50 wt. %, particularly preferably of 5 to 30 wt. %, very particularly preferably of 10 to 25 wt. %, relative to the total weight of the composition of the dosage form.

It is, of course, apparent to persons skilled in the art that the sum of all the components of the dosage form according to the invention must always be 100 wt. %.

The dosage forms according to the invention exhibit a release profile of the active ingredient clavulanic acid which corresponds to that of a tablet which has been produced from a dry mixture by press-molding. This is surprising because the prior art, in particular WO 01/66081 (page 12 et seq.) teaches that the use of sucrose fatty acid esters with a low HLB value, i.e. an HLB value of $\leq 3$, in the production of multiparticulate dosage forms containing active ingredients other than clavulanic acid or the salts thereof results in delayed release of the active ingredient. It was thus all the more surprising that this should not occur in the dosage form according to the invention containing clavulanic acid or a physiologically acceptable salt.

The dosage form according to the invention may preferably contain at least one physiologically acceptable, preferably anhydrous, auxiliary substance selected from among the group comprising lactose, microcrystalline cellulose, silicon dioxide (Aerosil or Syloid), kaolin, talcum, titanium dioxide, mannitol, $CaHPO_4$ and pH regulators, such as anhydrous citric acid, $Na_2HPO_4$ and ascorbic acid. Kaolin, $CaHPO_4$ and/or Syloid are particularly preferred. The auxiliary substances, like the active ingredient, must have any residues of water removed from them and be used in the driest possible form.

If at least one physiologically acceptable auxiliary substance is present in the dosage form according to the invention, said substance may preferably be used in a quantity of 1 to 60 wt. %, particularly preferably of 3 to 45 wt. %, very particularly preferably of 5 to 15 wt. %, relative to the total weight of the composition of the dosage form.

The multiparticulate dosage forms according to the invention are preferably present as granules, particularly preferably as pellets, such as melt-formulated granules or pellets, and may be packaged in this form in capsules, sachets, in a bottle and in a drinking straw with a barrier device and/or controller, as is described, for example, in WO 00/45888, the pertinent disclosure of which is incorporated herein by reference. They may also be press-molded into tablets.

The dosage forms according to the invention may surprisingly be produced by preferably anhydrous melt-formulation of the corresponding composition, without the storage stability of the dosage form according to the invention consequently being impaired. There were in fact grounds to fear that the input of heat required for melt-formulation would initiate decomposition of the clavulanic acid.

However, when stored with exclusion of moisture, the dosage forms according to the invention are as stable as the above-mentioned dry preparations.

The melt-formulated, multiparticulate dosage forms according to the invention, preferably corresponding pellets or granules, may thus be stored at room temperature and at elevated temperatures, such as for example 30° C. or 40° C. under ICH stability conditions, without there being any discoloration of the dosage form and reduction in active ingredient content brought about by decomposition of the clavulanic acid. This is the case when other binders conventional for melt granulation, such as for example polyethylene glycol, are used.

The present invention accordingly also provides a process for producing a multiparticulate dosage form according to the invention by preferably anhydrous melt-formulation of a mixture containing clavulanic acid and/or one of the physiologically acceptable salts thereof and at least one sucrose fatty acid ester and optionally at least one further physiologically acceptable auxiliary substance, wherein all components are preferably used in the predried state, i.e. as anhydrous as possible.

According to the invention, formulation of the melt is not taken to mean any kind of spinning of the molten composition of the dosage form according to the invention. Melt-formulation does, however, also include only softening of the binder component, sucrose fatty acid ester, without complete fusion, such that the dosage form according to the invention may also be produced, i.e. formulated, by sintering.

The multiparticulate dosage form according to the invention is preferably produced by at least partially softening the sucrose fatty acid ester component by input of energy to such an extent that it provides its binder action, optionally cooling it, mixing it with the clavulanic acid and/or with at least one of the physiologically acceptable salts thereof and at least one further, optionally present physiologically acceptable auxiliary substance, granulating the mixture, optionally rounding and cooling it, wherein mixing of the components and softening or melting may proceed in any desired order.

The process according to the invention is preferably performed under exclusion of moisture (relative atmospheric humidity of the surroundings less than 20%) and at a room or ambient temperature of below 25° C.

If a further auxiliary substance is present in the composition of the dosage form according to the invention, the auxiliary substance, preferably kaolin and/or Syloid, is mixed with the sucrose fatty acid ester component, the mixture is melted, cooled, mixed with the optionally heated clavulanic acid or the corresponding salt, the mixture is maintained during granulation at a product temperature of preferably 60° to 70° C. and the resultant melt-granules or the resultant melt-pellets are rapidly cooled.

The sucrose fatty acid component is softened or melted by optionally mixing it with further components, heating it to a temperature of 50 to 80° C., preferably of 55 to 75° C., particularly preferably of 60 to 65° C., and preferably cooling it again before granulation of the complete mixture is begun and carried out, preferably at these temperatures.

The granules containing clavulanic acid or the pellets obtained by rounding the granules are rapidly cooled directly after the production thereof, for example by means of direct addition of dry ice or introduction of liquid nitrogen into the reaction product, preferably to a temperature below the melting temperature of the sucrose fatty acid component used, preferably to a temperature of below 35° C.

Cooling preferably proceeds by introduction of liquid nitrogen which, on contact with the hot granules or the pellets, vaporises and spreads throughout the entire mass of granules so resulting in flash cooling, i.e. cooling within less than one minute, of the granules or pellets to temperatures of at most 30° C. This procedure additionally assists in ensuring the gentlest possible treatment of the clavulanic acid.

Double-walled high speed mixers may preferably be used for the entire production of the dosage form according to the invention by simultaneously or successively mixing all the components and performing heating, granulation and optionally subsequent pelletisation and cooling in said apparatus. Conventional commercially available high speed mixers, which are preferably operated at a peripheral speed of 7-15 m/sec, are used as the mixers.

To this end, rotational speeds in the range preferably from 800 to 2000 revolutions per minute, particularly preferably from 950 to 1050 revolutions per minute, are maintained for mixing the components and/or for granulation in the mixer and the chopper is preferably also operated at least until granules are obtained. The rotational speeds required depend on the size of the granulator and should be selected such that the above-stated peripheral speed is achieved. The period which elapses until granules or pellets are formed depends on mixer size, rotational speed and load level and is familiar to the person skilled in the art. Rounding of the granules may be achieved with the assistance of the mixer without also turning on the chopper.

The granules containing clavulanic acid and/or clavulanate obtained by the process according to the invention are surprisingly already virtually spherical without a separate downstream rounding step and are distinguished by a relatively narrow particle size distribution, i.e. ≧80% of the particles are in the range from 250 to 710 μm. The granules accordingly preferably already assume the form of pellets, such that no corresponding rounding is necessary. Size classification of the particles is determined by screening.

Tablets may also be produced from the melt-formed particles according to the invention by press-molding granules obtained according to the invention into tablets, or packaging them in sachets or capsules or in a drinking straw, as is disclosed in WO 00/54888.

It is furthermore possible, with the assistance of melt extruders, to heat the mixture of the components, which have already been mixed either outside the extruder or in the extruder, or granules, which have been produced as stated above, at least up to the softening point or until a melt is obtained, to perform extrusion and rapidly to cool the extruded strand as stated above and to chop it in conventional manner.

The multiparticulate, melt-formed dosage forms according to the invention may be provided in known manner with a coating, preferably for flavor masking. The coating material is preferably applied as a solution in an organic solvent or under aqueous conditions, as disclosed in WO 95/28927, or in a molten state.

The dosage forms according to the invention are furthermore ideally suitable for the preparation of a combination pharmaceutical preparation with a β-lactam antibiotic, preferably amoxicillin.

The present invention accordingly also provides a pharmaceutical preparation comprising the combination of the dosage form according to the invention of clavulanic acid and/or at least one corresponding physiologically acceptable salt and a separately formulated, oral, preferably multiparticulate dosage form of a β-lactam antibiotic. The β-lactam antibiotic preferably contains amoxicillin and/or a corresponding physiologically acceptable salt and/or solvate as the antibiotic, preferably a corresponding hydrate, very particularly preferably amoxicillin trihydrate.

As used herein the term "separately formulated" means that the antibiotic is not formulated together with the clavulanic acid to yield a dosage form, but is instead obtained in a distinct production or formulation process and, to produce the combined preparation, is packaged in a container, such as a capsule, a sachet or a drinking straw for administration to patients in the same manner as the separately formulated dosage forms containing clavulanic acid.

In the combination pharmaceutical preparation according to the invention, the ratio by weight of the clavulanic acid-containing dosage form according to the invention to the amoxicillin-containing dosage form, in each case respectively calculated on the basis of the free acid or as amoxicillin, amounts to 1:2 to 1:14, preferably 1:4 to 1:8, particularly preferably 1:4, 1:7 or 1:8.

The combination pharmaceutical preparation according to the invention is highly suitable for the treatment of bacterial infections. The present invention also provides the use of the melt-formulated, multiparticulate dosage forms according to the invention for producing a combination pharmaceutical preparation with a further separately formulated oral, preferably solid, multiparticulate dosage form of a β-lactam antibiotic, preferably amoxicillin, for the treatment of bacterial infections, preferably of bacterial infections in children, in particular for the treatment of otitis media, for the treatment of respiratory diseases in humans or for the treatment of urinary tract diseases.

The release profile of preparations produced in the Examples was determined as follows:

The preparations were placed in a paddle stirrer apparatus in accordance with the European Pharmacopoeia at a temperature of 37° C. and a rotational speed of 100 $min^{-1}$ or 150 $min^{-1}$ in 300 ml of artificial gastric juice (pH 2) for 10 minutes, whereby in the case of determination in artificial gastric juice the samples taken for measurement were rebuffered to a pH of greater than 5, in order to prevent decomposition of the clavulanic acid prior to the HPLC determination, or in 900 ml of artificial intestinal juice (pH 6.8) for 15 minutes. This pH value was maintained until the test. The quantity of the active ingredient clavulanic acid released at each point in time was determined by HPLC. The stated values are means values from in each case 6 samples.

The invention is explained in further detail below with reference to illustrative examples. These explanations are given merely by way of example and are not intended to restrict the overall scope of the invention.

EXAMPLES

Example 1

Pellets having the following composition were produced in a room with atmospheric humidity of less than 20% and a room temperature of below 25° C.:

| | |
|---|---|
| 50 g of sucrose stearate (di-, tri-, polyester/HLB 1) Melting range of 51 to 61° C. (sucrose ester S170) | 20 wt. % |
| 187.5 g of potassium clavulanate, mixed with microcrystalline cellulose (Avicel) 1:1 | 75 wt. % |
| 12.5 g of kaolin | 5 wt. % |
| | 100 wt. % |

The components are virtually anhydrous due to drying. A 2 liter mixer (Diosna), fitted with a chopper, was heated to 60° C. The sucrose stearic acid ester, kaolin and the mixture of potassium clavulanate with microcrystalline cellulose were placed in this mixer. The resultant powder mixture was mixed and granulated with heating at 1300 revolutions per minute mixing power with the chopper turned on at 2000 revolutions per minute chopper speed. Once the power uptake of the mixer blades had dropped, the chopper was turned off and the mixer operated for a further 3 minutes at the stated rotational speeds. The resulting pellets were cooled in a bowl cooled with dry ice. The pellets had a particle size distribution determined by screening of 3% of the pellets <250 μm, 88% 250 to 710 μm, 9%>710 μm.

The storage stability of the pellets containing clavulanic acid was tested by packaging the pellets in aluminium pouches directly after cooling, and the sealed pouches were stored at room temperature (25° C.) or at 30° C. or 40° C. Storage stability was ascertained by determining the content of potassium clavulanate by HPLC measurement. The corresponding stability data are listed in the following Table, entitled "Storage stability".

Example 2

Clavulanic acid pellets with the following composition were produced under the ambient conditions stated in Example 1:

| | |
|---|---|
| 457.2 g of sucrose stearate (mixture of di-, tri- and polyester/HLB 1/sucrose ester S-170) | 12.70 wt. % |
| 2685.6 g of potassium clavulanate (pure) | 74.60 wt. % |
| 457.2 g of kaolin | 12.70 wt. % |
| | 100 wt. % |

All components were anhydrous. Pellets with the above composition were produced by preheating a 25 liter Diosna mixer to 60° C. and then mixing the sucrose ester and kaolin at 650 revolutions per minute mixing power and 200 revolutions per minute chopper speed until the mixture was melted. The mixture was cooled to room temperature (25° C.) and added to the potassium clavulanate, which had been heated to approx. 60° C., and granulated and rounded at 65° C., 700 revolutions per minute mixing power and 1000 revolutions per minute chopper speed. The finished pellets were rapidly cooled within <3 min to 30° C. by introduction of liquid $N_2$ while occasionally being mixed without turning on the chopper. The resultant pellets exhibited a narrow size distribution, in which 18% of the pellets were <250 μm, 80% of the pellets were in the range from 250 to 710 μm, and 2% of the pellets were >710 μm.

Some of the pellets were packaged in aluminium pouches and the sealed pouches were stored at room temperature (25° C.), 30° C. or 40° C. in order to determine the stability of the clavulanic acid pellets. Stability data are stated in the following Table, entitled "Storage stability".

Release of the clavulanic acid from the pellets in gastric juice (pH 2) or in intestinal juice (pH 6.8) was as follows:

| | Min. | | | |
|---|---|---|---|---|
| | 1 | 5 | 10 | 15 |
| % clavulanic acid (pH 6.8) | 56.5 | 96.9 | 100 | 100 |
| % clavulanic acid (pH 2) | 56.5 | 82.9 | 100 | — |

Example 3

Clavulanic acid pellets having the following composition were produced under the ambient conditions stated in Example 1:

| | |
|---|---|
| 21.25 g of sucrose stearate (mixture of di-, tri- and polyester/HLB 1/sucrose ester S-170) | 17 wt. % |
| 78.25 g of potassium clavulanate mixed with 19.25 g of microcrystalline cellulose (Avicel pH 113) | 62.6 wt. % / 15.4 wt. % |
| 6.25 g of kaolin | 5 wt. % |
| | 100 wt. % |

All components were virtually anhydrous. Pellets having the above composition were produced in accordance with Example 2, whereby the mixing power was 1400 revolutions/minute and the chopper speed 300 revolutions/minute. The resultant pellets exhibited a size distribution of more than 80% of the pellets in a range from 250 to 710 μm.

100 g of the pellets were coated in a fluidized bed coater with glycerol distearate up to an application rate of 13% g/g at a product temperature of 40° C. The storage stability of the pellets coated in this manner was determined by measuring the clavulanic acid content of samples which were packed in aluminium pouches and stored at room temperature (25° C.), 30° C. and 40° C. The values are stated Table "Storage stability".

Example 4

Clavulanic acid pellets having the following composition were produced under the ambient conditions stated in Example 1:

| | |
|---|---|
| 38.35 g of sucrose stearate (mixture of di-, tri- and polyester/HLB 1/sucrose ester S-170) | 13 wt. % |
| 221.25 g of potassium clavulanate (pure) | 75 wt. % |
| 35.40 g of citric acid (anhydrous) | 12 wt. % |
| | 100 wt. % |

All components were anhydrous. Pellets having the above composition were produced by preheating a 2 liter Diosna mixer to 60° C. and then melting sucrose ester at 650 revolutions per minute mixing power and 200 revolutions per minute chopper speed. Potassium clavulanate and citric acid were added to the melted sucrose ester and granulated and rounded at 65° C., 700 revolutions per minute mixing power and 1000 revolutions per minute chopper speed. The finished pellets were rapidly cooled to <30° C. by introduction of liquid $N_2$ while occasionally being mixed without turning on the chopper. The resulting pellets exhibited a narrow size distribution, in which >80% of the pellets were in the range from 250 to 710 μm. The storage stability of the pellets stored in aluminium pouches was tested as described in Example 1. The values are shown in the Table "Storage stability".

Example 5

Clavulanic acid pellets with the following composition were produced under the ambient conditions stated in Example 1:

| | |
|---|---|
| 38.35 g of sucrose stearate (mixture of di-, tri- and polyester/HLB 1/sucrose ester S-170) | 13 wt. % |
| 221.25 g of potassium clavulanate (pure) | 75 wt. % |
| 11.80 g of kaolin | 4 wt. % |
| 11.80 g of citric acid, anhydrous | 4 wt. % |
| 11.80 g of sodium carbonate | 4 wt. % |
| | 100 wt. % |

All components were anhydrous. Pellets having the above composition were produced by preheating a 2 liter Diosna mixer to 60° C. and then mixing sucrose ester and kaolin at 650 revolutions per minute mixing power and 200 revolutions per minute chopper speed until the mixture was melted. Potassium clavulanate, citric acid and sodium carbonate were added to the mixture and granulated and rounded at 65° C., 700 revolutions per minute mixing power and 1000 revolutions per minute chopper speed. The finished pellets were rapidly cooled to 30° C. by introduction of liquid $N_2$ while occasionally being mixed without turning on the chopper. The resulting pellets exhibited a narrow size distribution, in which 80% of the pellets were in the range from 250 to 710 μm. The storage stability of the pellets stored in an aluminium pouch is shown in the Table "Storage stability".

Example 6

Clavulanic acid pellets having the following composition were produced under the ambient conditions stated in Example 1, with each dose containing 125 mg of clavulanic acid:

| | |
|---|---|
| 75.44 mg of sucrose stearate (mixture of di-, tri- and polyester/HLB 1/sucrose ester S-170) | 19 wt. % |
| 148.90 mg of potassium clavulanate (pure) | 37.5 wt. % |
| 86.36 mg of kaolin | 21.75 wt. % |
| 86.36 mg of hydrated silicon dioxide (Syloid AL-1-FP) | 21.75 wt. % |

Batch size was 600 g. Pellets having the above composition were produced by preheating a 4 liter Diosna mixer to 60° C. and then mixing sucrose ester and kaolin at 650 revolutions per minute mixing power and 1000 revolutions per minute chopper speed until the mixture was melted. The mixture was cooled to room temperature (25° C.) and added to the mixture of potassium clavulanate and $SiO_2$, which had been heated to approx. 60° C., and granulated and rounded at 65° C., 500-700 revolutions per minute mixing power and 1000 revolutions per minute chopper speed. The finished pellets were rapidly cooled within <3 min to 30° C. by introduction of liquid $N_2$ while occasionally being mixed without turning on the chopper. The resulting pellets exhibited a narrow size distribution, in which 18% of the pellets were <250 μm, 80% of the pellets were in the range from 250 to 710 μm, and 2% of the pellets were >710 μm.

Example 7

Clavulanic acid pellets having the following composition were produced under the ambient conditions stated in Example 1, with each dose containing 125 mg of clavulanic acid:

| | |
|---|---|
| 40.61 mg of sucrose stearate (mixture of di-, tri- and polyester/HLB 1/sucrose ester S-170) | 12 wt. % |
| 148.9 mg of potassium clavulanate (pure) | 44 wt. % |
| 148.9 mg of $CaHPO_4$ | 44 wt. % |
| | 100 wt. % |

Batch size was 600 g. All components were anhydrous. Pellets having the above composition were produced by preheating a 4 liter Diosna mixer to 60° C. and then mixing sucrose ester and a proportion of the $CaHPO_4$ at 650 revolutions per minute mixing power and 1000 revolutions per minute chopper speed until the mixture was melted. This mixture was cooled to room temperature (25° C.) and added to the mixture of potassium clavulanate, and the remainder of the $CaHPO_4$, which had been heated to approx. 60° C., and granulated and rounded at 65° C., 500 revolutions per minute mixing power and 1000 revolutions per minute chopper speed. The finished pellets were rapidly cooled within <3 min to 30° C. by introduction of liquid $N_2$ while occasionally being mixed without turning on the chopper. The resulting pellets exhibited a narrow size distribution, in which 18% of the pellets were <250 μm, 80% of the pellets were in the range from 250 to 710 μm, and 2% of the pellets were >710 μm.

Some of the pellets were packaged in drinking straws according to WO 00/45888 and stored in sealed vials at room temperature (25° C.), 30° C. or 40° C. in order to determine the stability of the clavulanic acid pellets. Stability data are stated in the following Table, entitled "Storage stability".

Release of the clavulanic acid from the pellets in gastric juice (pH 2) at 37° C./100 rpm determined by HPLC was as follows:

| | Min. | | |
|---|---|---|---|
| | 1 | 5 | 10 |
| % clavulanic acid | 49.0 | 82.0 | 84.5 |

Release in intestinal juice (pH 6.8) at 37° C./150 rpm was:

| | Min. | | | |
|---|---|---|---|---|
| | 1 | 5 | 10 | 15 |
| % clavulanic acid | 41.3 | 88.2 | 101 | 101 |

Example 8

Clavulanic acid pellets having the following composition were produced under the ambient conditions stated in Example 1, with each dose containing 125 mg of clavulanic acid:

| | |
|---|---|
| 44.5 mg of sucrose stearate (mixture of di-, tri- and polyester/HLB 1/sucrose ester S-170) | 13 wt. % |
| 148.90 mg of potassium clavulanate (pure) | 43.5 wt. % |
| 74.45 mg of kaolin | 21.75 wt. % |
| 74.45 mg of lactose monohydrate (grade 230) | 21.75 wt. % |

Batch size was 600 g. Pellets having the above composition were produced by preheating a 4 liter Diosna mixer to 60° C. and then mixing sucrose ester and a proportion of the kaolin at 650 revolutions per minute mixing power and 1000 revolutions per minute chopper speed until the mixture was melted. This mixture was cooled to room temperature (25° C.) and added to the mixture of potassium clavulanate, lactose and the remainder of the kaolin, which had been heated to approx. 60° C., and granulated and rounded at 65° C., 500 revolutions per minute mixing power and 1000 revolutions per minute chopper speed. The finished pellets were rapidly cooled within <3 min to 30° C. by introduction of liquid $N_2$ while occasionally being mixed without turning on the chopper. The resulting pellets exhibited a narrow size distribution, in which 18% of the pellets were <250 μm, 80% of the pellets were in the range from 250 to 710 μm, and 2% of the pellets were >710 μm.

The stability the clavulanic acid pellets was determined by storing some of the pellets as described in Example 7. Stability data are stated in the following Table entitled "Storage stability".

Release of the clavulanic acid from the pellets in intestinal juice (pH 6.8) at 37° C./150 rpm determined by HPLC was as follows:

| | Min. | | | |
|---|---|---|---|---|
| | 1 | 5 | 10 | 15 |
| % clavulanic acid | 41.8 | 88.4 | 98.3 | 100 |

Example 9

Clavulanic acid pellets having the following composition were produced under the ambient conditions described in Example 1, with each dose containing 125 mg of clavulanic acid:

| | |
|---|---|
| 44.5 mg of sucrose stearate (mixture of di-, tri- and polyester/HLB 1/sucrose ester S-170) | 13 wt. % |
| 148.9 mg of potassium clavulanate (pure) | 43.5 wt. % |
| 74.45 mg of kaolin | 21.75 wt. % |
| 74.45 mg of $CaHPO_4$ | 21.75 wt. % |

All components were anhydrous. Pellets having the above composition were produced by preheating a 4 liter Diosna mixer to 60° C. and then mixing sucrose ester and kaolin at 650 revolutions per minute mixing power and 1000 revolutions per minute chopper speed until the mixture was melted. The mixture was cooled to room temperature (25° C.) and added to the mixture of potassium clavulanate and $CaHPO_4$, which had been heated to approx. 60° C., and granulated and rounded at 65° C., 700 revolutions per minute mixing power and 1000 revolutions per minute chopper speed. The finished pellets were rapidly cooled within <3 min to 30° C. by introduction of liquid $N_2$ while occasionally being mixed without turning on the chopper. The resulting pellets exhibited a narrow size distribution, in which 18% of the pellets were <250 μm, 80% of the pellets were in the range from 250 to 710 μm, and 2% of the pellets were >710 μm.

The stability the clavulanic acid pellets was determined by storing some of the pellets as described in Example 7. Stability data are stated in the following Table, entitled "Storage stability".

Release of the clavulanic acid from the pellets in intestinal juice (pH 6.8) at 37° C./150 rpm determined by HPLC was as follows:

| | Min. | | | |
|---|---|---|---|---|
| | 1 | 5 | 10 | 15 |
| % clavulanic acid | 41.5 | 87.4 | 97.3 | 100 |

| | | Storage stability | | |
|---|---|---|---|---|
| Example | Initial conc.* % | 25° C. Content %** | 30° C. Content %** | 40° C. Content %** |
| 1 | 104 | — | 3 months 104.2 | 1 month 105 |
| 2 | 103.6 | 1 month 103.1 | 1 month 101.4 | 1 month 100.9 |
| | | 3 months 103.4 | 3 months 103.3 | 3 months 102.4 |
| 3 | 100.6 | 6 months 102.8 | 6 months 104.7 | 1 month 99.8 |
| | | | 18 months 98.2 | 6 months 100.2 |
| 4 | 96.4 | | | 1 month 95.7 |
| 5 | 96.9 | | | 1 month 96.1 |
| 7 | 98.3 | 3 months 99.4 | 3 months 101.8 | 3 months 99.8 |
| 8 | 102 | 3 months 100.0 | 3 months 99.9 | 3 months 97.6 |
| 9 | 98.3 | — | — | 1 month 103.1 |

*Initial concentration of clavulanic acid determined by HPLC.
**Concentration of clavulanic acid measured with HPLC after the stated storage time at the stated temperature.

Example 10

A bioequivalence study relative to Augmentin™ sachets containing amoxicillin/clavulanic acid (1000 mg/125 mg) was carried out using the pellets obtained from Example 2 containing 125 mg of clavulanic acid, which were packaged in a drinking straw with separately formulated pellets containing amoxicillin (1000 mg). Twelve test subjects participated in this study, the test and reference being administered in accordance with a crossover trial design. For the purpose of administration, the sachets were suspended in 200 ml of water for approx. 10 minutes, the clavulanic acid dissolving completely. This suspension was then administered to the test subjects. The pellets packaged in the drinking straw were taken by the test subjects with the assistance of 200 ml of water. The reference used was Augmentin™ sachets from France with a dosage of 1000 mg of amoxicillin to 125 mg of clavulanate, i.e. in a ratio of 8:1. The relative bioavailability the test formulation relative to the reference is shown in the following Table:

| Clavulanic acid (125 mg) pellets in a drinking straw relative to Augmentin ™ sachets | |
|---|---|
| $C_{max}$ | 93% |
| AUC | 94% |

The availability of the clavulanic acid from pellets according to the invention is comparable with that of the clavulanic acid solution of the reference product, i.e. the solid dosage form in the form of pellets exhibits in vivo release and comparable in vivo stability such that it is bioequivalent to a clavulanic acid reference administered as a solution.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A melt-formulated, multiparticulate granule or pellet, oral dosage form comprising clavulanic acid or at least one physiologically acceptable salt thereof, and at least one sucrose fatty acid ester, wherein the sucrose fatty acid ester is in an amount from 10-25% by weight relative to the total weight of the dosage form, is derived from a saturated or unsaturated $C_{12-22}$ fatty acid, has a melting range of 50-80° C. and has an HLB value of less than or equal to 3; and wherein the dosage form releases 100% of the clavulanic acid within 15 minutes or less when placed in artificial intestinal fluid at a pH of 6.8.

2. A dosage form according to claim 1, further comprising at least one physiologically acceptable auxiliary substance.

3. A dosage form according to claim 1, comprising at least one of potassium clavulanate and sodium clavulanate.

4. A dosage form according to claim 1, comprising potassium clavulanate.

5. A dosage form according to claim 1, containing from 1 to 90 wt. % of clavulanate, calculated as free acid, relative to the total weight of the dosage form.

6. A dosage form according to claim 5, containing from 30 to 80 wt. % of clavulanate, calculated as free acid, relative to the total weight of the dosage form.

7. A dosage form according to claim 1, comprising at least one mono-, di-, tri- or poly-ester of sucrose with at least one fatty acid.

8. A dosage form according to claim 7, comprising a mixture mono-, di-, tri- and poly-esters of sucrose with at least one fatty acid.

9. A dosage form according to claim 1, wherein the at least one sucrose fatty acid ester is derived from saturated $C_{12}$-$C_{22}$ fatty acids.

10. A dosage form according to claim 1, wherein the at least one sucrose fatty acid ester is derived from at least one of stearic acid and palmitic acid.

11. A dosage form according to claim 1, wherein the sucrose fatty acid ester has an HLB value of less than or equal to 2.

12. A dosage form according to claim 11, wherein the sucrose fatty acid ester has an HLB value of about 1.

13. A dosage form according to claim 1, wherein the at least one sucrose fatty acid ester has a melting range of 55° C. to 65° C.

14. A dosage form according to claim 1, wherein the at least one sucrose fatty acid ester has no influence on release of the clavulanic acid.

15. A dosage form according to claim 2, wherein said at least one physiologically acceptable auxiliary substance is selected from the group consisting of water-soluble fillers, water-insoluble fillers, and nucleating agents.

16. A dosage form according to claim 2, comprising at least one auxiliary substance selected from the group consisting of lactose, microcrystalline cellulose, silicon dioxide, $CaHPO_4$, kaolin, talcum, titanium dioxide, mannitol, and pH regulators.

17. A dosage form according to claim 16, comprising at least one auxiliary substance selected from the group consisting of kaolin, $CaHPO_4$ and silicon dioxide, and a pH regulator selected from the group consisting of citric acid, $Na_2HPO_4$ and ascorbic acid.

18. A dosage form according to claim 2, wherein the at least one physiologically acceptable auxiliary substance amounts to 1 to 60% by weight relative to the total weight of the dosage form.

19. A dosage form according to claim 18, wherein the at least one physiologically acceptable auxiliary substance amounts to 3 to 45% by weight relative to the total weight of the dosage form.

20. A dosage form according to claim 18, wherein the at least one physiologically acceptable auxiliary substance amounts to 5 to 15% by weight relative to the total weight of the dosage form.

21. A dosage form according to claim 1, wherein the dosage form is in the form of melt-granules or melt-pellets.

22. A dosage form according to claim 1, wherein the dosage form is packaged in a capsule, a sachet, a bottle or a drinking straw or is press-molded into a tablet.

23. A process for producing a dosage form according to claim 1, said process comprising:
   at least partially softening the sucrose fatty acid ester by energy input to such an extent that it provides a binder action;
   optionally cooling the softened sucrose fatty acid ester;
   mixing the softened sucrose fatty acid ester with the clavulanic acid or at least one physiologically acceptable salt thereof and optionally one or more physiologically acceptable auxiliary substances, and
   granulating the resulting mixture, and
   optionally rounding and cooling the granules,
wherein the mixing and energy input may proceed in any desired time sequence.

24. A process according to claim 23, wherein the sucrose fatty acid ester component is optionally mixed with an auxiliary substance, melted and cooled, the cooled component or mixture is mixed with the optionally heated clavulanic acid, is partially melted with energy input, is granulated, and is optionally rounded and cooled.

25. A process according to claim 23, wherein the clavulanic acid or salt and the optional auxiliary substances are heated to a temperature of 50° C. to 80° C. prior to granulation.

26. A process according to claim 25, wherein the clavulanic acid or salt and the optional auxiliary substances are heated to a temperature of 60° C. to 65° C. prior to granulation.

27. A process according to claim 23, further comprising rapidly cooling the clavulanic acid-containing granules or pellets directly after production thereof by addition of dry ice or by introduction of liquid nitrogen.

28. A dosage form obtained by the process of claim 23.

29. A combination of two separate pharmaceutical preparations said combination consisting of a first separately formulated dosage form according to claim 1 and a separately formulated second oral dosage form comprising at least one β-lactam antibiotic.

30. A preparation according to claim 29, wherein said β-lactam antibiotic is amoxicillin.

31. A preparation according to claim 30, wherein the amoxicillin is present in the form a physiologically acceptable salt, or as a hydrate.

32. A preparation according to claim 29, wherein the weight ratio of the clavulanic acid-containing dosage form calculated on the basis of the free clavulanic acid to the β-lactam antibiotic-containing dosage form calculated on the basis of the β-lactam antibiotic is in the range from 1:2 to 1:14.

33. A preparation according to claim 32, wherein the weight ratio of the clavulanic acid-containing dosage form calculated on the basis of the free clavulanic acid to the β-lactam antibiotic-containing dosage form calculated on the basis of the β-lactam antibiotic is in the range from 1:4 to 1:8.

34. A method of treating a bacterial infection, said method comprising administering to a bacterially infected patient an effective anti-bacterial amount of a preparation according to claim 29.

35. A method according to claim 34, wherein said patient is a human afflicted with otitis media or a respiratory infection or a urinary tract infection.

* * * * *